US006410041B1

(12) United States Patent
Lewis et al.

(10) Patent No.: US 6,410,041 B1
(45) Date of Patent: Jun. 25, 2002

(54) CULTURING CELLS IN PRESENCE OF AMPHIPATHIC WEAK BASES AND/OR CATIONS AND MULTIPLE DRUG RESISTANCE INHIBITOR CONTAINING RESERPINE

(75) Inventors: Kim Lewis, Newton; Peichun Hsieh, Cambridge, both of MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 09/067,873

(22) Filed: Apr. 28, 1998

(51) Int. Cl.[7] .................. A01N 25/00; A01N 43/48; A01N 63/00; A01N 65/00; C12N 1/00

(52) U.S. Cl. .................. 424/405; 424/93.1; 435/243; 435/317.1; 435/822; 514/254.09; 514/279; 514/280; 514/359; 514/415

(58) Field of Search .................. 424/93.1, 405; 435/822, 243, 317.1, 800; 514/1, 254.09, 279, 280, 359, 415

(56) References Cited

U.S. PATENT DOCUMENTS

| | | | | |
|---|---|---|---|---|
| 4,708,861 A | * | 11/1987 | Popesca et al. ............... 424/1.1 |
| 5,165,922 A | | 11/1992 | Hellstrom et al. ........ 424/155.1 |
| 5,182,293 A | | 1/1993 | Sunkara et al. .............. 514/340 |
| 5,489,519 A | | 2/1996 | Deeley et al. .............. 435/69.1 |
| 5,510,239 A | | 4/1996 | Baracchini, Jr. et al. ......... 435/6 |
| 5,525,232 A | * | 6/1996 | Veiro et al. .................. 210/638 |
| 5,543,428 A | | 8/1996 | Sawyer et al. .............. 514/456 |
| 5,567,592 A | | 10/1996 | Benet et al. ................ 435/7.21 |
| 5,571,687 A | | 11/1996 | Casey et al. .................... 435/29 |
| 5,643,761 A | | 7/1997 | Fisher et al. ................ 435/91.1 |
| 5,646,011 A | | 7/1997 | Yokoyama ................. 435/69.1 |
| 5,650,321 A | | 7/1997 | Levy ........................ 435/252.3 |
| 5,670,507 A | | 9/1997 | Rice et al. ............. 514/263.35 |
| 5,683,987 A | | 11/1997 | Smith ........................... 514/44 |
| 5,714,320 A | | 2/1998 | Kool ............................. 435/6 |
| 5,717,092 A | | 2/1998 | Armistead et al. .......... 544/129 |
| 5,723,459 A | | 3/1998 | Armistead et al. ........ 514/237.8 |
| 5,744,485 A | | 4/1998 | Zelle et al. .................. 514/318 |
| 5,766,880 A | | 6/1998 | Deeley et al. .............. 435/69.1 |
| 5,766,924 A | | 6/1998 | Levy ........................ 435/252.3 |
| 5,783,431 A | | 7/1998 | Peterson et al. ............. 435/455 |
| 5,789,184 A | | 8/1998 | Fowlkes et al. ............ 435/7.31 |
| 5,965,434 A | * | 10/1999 | Wolf et al. ............... 435/320.1 |
| 6,027,888 A | * | 2/2000 | Georgiou et al. .............. 435/6 |
| 6,093,816 A | * | 7/2000 | Lin et al. ..................... 544/122 |

FOREIGN PATENT DOCUMENTS

| | | |
|---|---|---|
| JP | 08268806 A * | 10/1996 |
| WO | WO 95/21381 | 8/1995 |
| WO | WO 97/40358 | 10/1997 |

OTHER PUBLICATIONS

JP Abstr. (English), Oct. 1996.*
Ahmed, M, et al., "Protein that Activates Expression of Multidrug Efflux Transporter upon Binding the Transporter Substrates", *The Journal of Biological Chemistry*, vol. 269, No. 45, Issue of Nov. 11 pp. 28506–28513, (1994).
Bolhuis, H., et al., "Mechanisms of multidrug transporters", *FEMS Microbiology Reviews*, vol. 21, pp. 55–84, (1997).
Desnottes, Jean–Francois, "New Targets and Strategies for the Development of Antibacterial Agents," *Tibtech*, vol. 14, Apr. (1996).
Kluytmans, J. et al, "Nasal Carriage of *Staphylococcus aureus*: Epidemiology, Underlying Mechanisms, and Associated Risks," *Clinical Microbiology Reviews*, pp. 505–520, vol. 10, No. 3 Jul. (1997).
Krulwich, T. et al, "Energetic Problems of Extremely Alkaliphilic Aerobes," *Biochimica et Biophysica Acta 1275* pp. 21–26 (1996).
Lewis, Kim, "Multidrug Resistance Pumps in Bacteria: Variations on a Theme," *TIBS 19* pp. 119–123, Mar. (1994).
Ma, D. et al, "Molecular Cloning and Characterization of acrA and acrE Genes of *Escherichia coli,* "*Joural of Bacteriology*, p. 6299–6313, Oct. (1993).
Neyfakh, A. et al, "Fluoroquinolone Resistance Protein NorA of *Staphylococcus aureus* is a Multidrug Efflux Transporter," *Antimicrobial Agents and Chemotherapy*, pp. 128–129, Jan. (1993).
Ng, E. et al, Quinolone Resistance Mediated by norA: Physiologic Characterization and Relationship to flqB, a Quinolone Resistance Locus on the *Staphylococcus aureau* Chromosome, *Antimicrobial Agents and Chemotherapy*, pp. 1345–1355, Jun. (1994).

(List continued on next page.)

*Primary Examiner*—David M. Naff
*Assistant Examiner*—Deborah Ware
(74) *Attorney, Agent, or Firm*—Dana M. Gordon; Foley, Hoag & Eliot LLP

(57) ABSTRACT

Methods are provided relating to the enhanced cytoplasmic accumulation of amphipathic weakly basic or amphipathic cationic molecules in prokaryotes and eukaryotes under conditions of high extracellular pH. Furthermore, the methods relate to the unexpected synergistic effects of high extracellular pH and disrupted cellular efflux mechanisms on the cytoplasmic accumulation of amphipathic weakly basic or amphipathic cationic molecules in prokaryotes and eukaryotes. Methods are also provided for increasing the therapeutic potency of amphipathic weakly basic or amphipathic cationic compounds, e.g. antiseptics and disinfectants by using the antiseptic or disinfectant in the presence of a multiple drug resistance inhibitor such as reserpine. Finally, methods also relate to the exploitation of the aforementioned discoveries in the screening of small molecules, and libraries thereof, for biological activity in prokaryotes and eukaryotes. Also provided is a formulation comprising an amphipathic weak base, an amphipathic cation, or both, and a multiple drug resistance inhibitor wherein the pH of the formulation is 9.0. Furthermore, the combination of these ingredients have antiseptic and/or disinfectant effects.

30 Claims, No Drawings

OTHER PUBLICATIONS

Padan, E. et al, "Molecular Biology of NA$^+$/H$^+$ Antiporters: Molecular Devices that Couple the Na$^+$ and H$^+$ Circulation in Cells," *Biochimica et Biophysica Acta*, 1187 (1994), pp. 206–210.

Paulsen, I. et al, "Proton–Dependent Multidrug Efflux Systems," *Microbiological Reviews*, pp. 575–608, vol. 60, No. 4, Dec. (1996).

Strohl, William, "Industrial Antibiotics: Today and the Future," *Biotechnology of Antibiotics*, Marcel Sekker, Inc., New York, Strohl, W.R., editor.

Tennent, J. et al, Physical and Biochemical Characterization of the qacA Gene Encoding Antiseptic and Disinfectant Resistance in *Staphylococcus aureus, Journal of General Microbiology*, 135, 1–10 (1989).

Yamada, H. et al, Quinolone Susceptibility of norA–Disrupted *Staphylococcus aureas, Antimicrobial Agents and Chemotherapy*, p. 2308–2309, Oct. (1997).

\* cited by examiner

CULTURING CELLS IN PRESENCE OF AMPHIPATHIC WEAK BASES AND/OR CATIONS AND MULTIPLE DRUG RESISTANCE INHIBITOR CONTAINING RESERPINE

GOVERNMENT FUNDING

Work described herein was supported in part with funding from the National Institutes of Health. The United States Government has certain rights in this invention.

BACKGROUND OF THE INVENTION

Multidrug resistance (MDR), the principle mechanism by which pathogens manifest resistance to biologically active agents, is a major public health challenge. The multidrug resistance phenotype is dependent upon the expression of enzymes that degrade specific classes of cytotoxic agents, and/or molecular pumps that are capable of expelling exogenous agents from the cytoplasm of bacterial, fungal and mammalian cells. Moreover, the expression of MDR in bacterial, fungal and malignant cells poses obstacles for the process of drug discovery. Assays designed to screen compounds, or libraries thereof, may fail to reveal the presence of active constituents due to the presence of MDR in the cell lines of the assays. This phenomenon is certain to leave undiscovered new, and potentially highly beneficial, drug candidates. At the very least, the various mechanisms of MDR undermine the efficacy of known cytostatic and/or cytotoxic compounds.

Pathogenic bacteria continue to be a major source of disease in humans and animals. Improvements in minimizing bacterial contamination have made substantial inroads in eradicating or containing the spread of bacterial disease. Many bacterial infections can be effectively treated in the acute phase of infection with antibiotics. There are, however, a large number of diseases that escape early detection and don't respond to antibiotic treatment. Added to this is the possibility of misdiagnosis, inavailability of medical care, development of antibiotic resistant organisms or asymptomatic primary infection. Many bacterial and parasitic diseases are endemic to certain regions of the world; in particular, the tropics and sub-tropics. The problem is exacerbated in those areas suffering from inadequate water and sewage treatment. The need for new antibacterials is due predominantly to two factors: the spread of antibiotic resistance genes; and the posture adopted by major pharmaceutical firms during the 1970s and 1980s that the market for new antibiotics had permanently diminished.

Antimicrobial resistance continues to spread in nosocomial pathogens in acute care hospitals and other key settings of managed health care systems. Appropriate control measures for such resistant organisms depend, in part, on the pathways by which resistance has arisen. Unfortunately, these pathways differ greatly from organism to organism and setting to setting. Although the epidemiology of resistant organisms sometimes is similar to that of susceptible organisms of the same kind, in some situations it may be quite different. Bacterial MDR pumps that expel known disinfectants have made it more difficult to sterilize hospital settings. Likewise, bacterial MDR pumps have undermined the effectiveness of antiseptics and antibiotics.

Acquired resistance to chemotherapy is a major problem in treatment of cancer by conventional cytotoxic drugs. Tumors may initially respond well to chemotherapy but later become resistant to a variety of unrelated drugs, leading to relapse. MDR in malignant cells is largely dependent on the expression of one or the other or both of two genes: mdr1 and mrp. These genes encode transmembrane energy-dependent molecular "pumps" that expel a wide variety of anticancer agents from malignant cells (Grant et al., Cancer Res. 54: 357–361, 1994). The normal functions of these molecular pumps are not well defined, but both are expressed by hematopoietic cells; P-gp, additionally, has been shown to have a causal role in immunofunction (Gupta et al., J. Clin. Immunol. 12: 451–458, 1992). The MRP is a molecular pump initially found to be involved in MDR in lung cancer, and then later found to be expressed in other cancer types. This protein is overexpressed in certain tumor cell lines which are multidrug resistant but do not overexpress P-glycoprotein (Cole et al. (1992) Science 258:1650–1654; Slovak et al., (1993) Cancer Res. 53:3221–3225). P-gp is a molecular pump long known to be involved in producing multidrug resistance in many tumor types (Chin et al., Adv. Cancer Res. 60: 157–180, 1993; Cole et al., Science 258: 1650–1654, 1992; Grant et al., Cancer Res. 54: 357–361, 1994; Krishnamachary and Center, Cancer Res. 53: 3658–3661, 1993; Zaman et al., Cancer Res. 53: 1747–1750, 1993).

Studies in which inhibitors of bacterial MDR pumps or P-gp inhibitors were administered to resistant bacterial or malignant cells, respectively, have shown that such competitive inhibitors can increase the response of the target cells to cytotoxic pharmaceutical agents. For example, MDR malignant cells are rendered more sensitive, under the aforementioned conditions, to the cytotoxic agents without an equivalent increase in the sensitivity of surrounding normal tissues.

In a second approach to attenuating the multidrug pumps, either bacterial or mammalian, oligonucleotides, or analogues thereof, are administered that are designed to block at the level of translation the expression of the genes that code for the pumps. These antisense oligonucleotides have several features which make them clinically attractive. Success in the area of chemotherapy illustrates this point: There are reports in the literature of reduced drug resistance in cultured cell lines following treatment with oligonucleotides targeting MDR-1 mRNA. Thierry et al. (Biochem. Biophys. Res. Comm. 190: 952–960, 1993) report a oligonucleotide 15-mer that gave 95% inhibition of MDR-1 expression when encapsulated in liposomes; this effect was associated with a 4-fold increase in sensitivity of the tumor cells to doxorubicin. When this 15-mer was administered without liposomes, inhibition of MDR1 expression was only 40% of control values. Jaroszewski et al. (Cancer Comm. 2: 287–294, 1990) and Corrias and Tonini (Anticancer Res. 12: 1431–1438, 1992) both found inhibition with only one out of five candidate oligonucleotides. Jaroszewski et al. describe a phosphorothioate that gave 25% reduction in P-gp expression at 15 $\mu$M and 33% reduction at 30 $\mu$M when incubated with MCF-7/ADR breast cancer cells for 5 days. This reduction in P-gp expression was associated with a small increase in the doxorubicin sensitivity of the cells (20% increase in cell death when 10 $\mu$M of the oligonucleotide was used). Corrias & Tonini report a phosphodiester oligonucleotide that gave only a slight reduction in P-gp at 30 $\mu$M when incubated for 36 h with doxorubicin-resistant colon adenocarcinoma cells. The reduction in P-gp expression was associated with a significant increase in the in vitro sensitivity of the cells to the cytotoxic effects of doxorubicin (80% and 53% dose reductions in $IC_{50}$, respectively).

The process of drug discovery can be hampered by the presence of MDR phenotypes in bacteria, fungi, and malignancies. These phenotypes may be expressed in the organisms and cell lines exploited for in vitro screening of new drug candidates; more importantly, over time the MDR phenotype can evolve "unnoticed" in a cell line used for in vitro assays. This situation would lead to false negatives, and thereby leave undiscovered potentially rewarding new leads. This situation impacts the discovery of new lead compounds; compounds that would otherwise be cytotoxic are made to appear inactive in assays by the underlying mechanisms of MDR. A means of reliably separating these variables promises to provide new lead compounds active against bacterial infections, fungal infections, and cancer. Additionally, similar logic may be applied to the discovery of so-called chemosensitizers, compounds that disrupt the MDR phenotype but are not themselves cytotoxic.

SUMMARY OF THE INVENTION

The present invention relates to the enhanced cytoplasmic accumulation of amphipathic weakly basic or amphipathic cationic molecules in prokaryotes and eukaryotes under conditions of high extracellular pH. Furthermore, the present invention relates to the unexpected synergistic effects of high extracellular pH and disrupted cellular efflux mechanisms on the cytoplasmic accumulation of amphipathic weakly basic or amphipathic cationic molecules in prokaryotes and eukaryotes. The present invention relates to methods for increasing the therapeutic potency of amphipathic weakly basic or amphipathic cationic compounds, e.g. antiseptics and disinfectants. Finally, the present invention relates to the exploitation of the aforementioned discoveries in the screening of small molecules, and libraries thereof, for biological activity in prokaryotes and eukaryotes.

The present invention may be applied to the discovery of new cytotoxic agents. These agents may be active against bacteria, fungi, and/or malignant cells. Additionally, the present invention may be exploited in the search for chemosensitizers of resistant bacteria, fungi, and/or malignant cells.

DETAILED DESCRIPTION OF THE INVENTION

I. Overview

The subject methods are based, at least in part, on three observations. First, that a mutant of S. aureus with a knockout in the norA gene coding an MDR pump has substantially increased sensitivity to a large number of antimicrobials. Second, that increasing the pH of the medium favors the accumulation of amphipathic weakly basic or amphipathic cationic substances in cells. Third, that there is a synergistic interaction, resulting in enhancements of sensitivity of up to 1,000-fold, between the norA gene knockout and high extracellular pH. The subject methods may be applied in a number of embodiments. In general, the present invention provides: 1) methods for sensitive drug screens in both prokaryotic and eukaryotic cells; 2) methods for the discovery of antagonists of MDR in both prokaryotic and eukaryotic cells; 3) methods for the discovery of new activities of known compounds, e.g. plant alkaloids; 4) agricultural and/or pharmaceutical formulations of compounds pinpointed by the subject methods; and 5) methods for increasing the therapeutic potency of amphipathic weakly basic or amphipathic cationic compounds, e.g. antiseptics and disinfectants.

In certain embodiments, cells—under conditions wherein some or all of their endogenous MDR mechanisms are disrupted—are incorporated into assays for compounds with a desired effect on that cell line. This assay system may additionally incorporate a high pH medium to increase the cytoplasmic accumulation of amphipathic weakly basic or amphipathic cationic compounds. Alternatively, this assay system may additionally incorporate a low pH medium to increase the cytoplasmic accumulation of amphipathic weakly acidic compounds.

In general, charged molecules do not easily cross the cellular membranes of prokaryotes or eukaryotes. This fact is due, in part, to the hydrophobic nature of cellular membranes and the so-called membrane potential. If the proportion of the charge-neutral form of a amphipathic weakly acidic or amphipathic weakly basic molecule can be increased, e.g. by adjustment of the pH of the external medium, greater quantities of that molecule will be able to cross the cellular membranes of resident organisms (see, inter alia: Webb et al. *Antimicrobial Agents and Chemotherapy* 1998, 42, 45–52; and references contained therein). In a pH neutral medium, the cytoplasm of a cell is slightly alkaline relative to the medium; the resulting pH gradient across the cell membrane drives extrusion of amphipathic weak bases from the cytoplasm. In a high pH medium (pH ~9), the pH gradient across the cell membrane is inverted thereby reversing the direction of flux of amphipathic weak bases. Additionally, in a high pH medium (pH ~9), the cellular membrane potential is increased and this change leads to an increase in the accumulation of amphipathic cations, e.g. quaternary ammonium ions, in the cytoplasm.

Numerous mechanisms of MDR are known. Chief among these mechanisms are the efflux pumps (MDR pumps) and the expression of enzymes that degrade or modify exogenous compounds to produce inactive, or substantially less active, compounds. Antagonism of an enzyme, or enzymes, responsible for the inactivation of an exogenous compound allow that compound to exert its effect on the target cell line to a greater extent. Disruption in an organism of an operating MDR pump will increase the cytoplasmic accumulation of compounds that are subject to that pump. A given mode of MDR may theoretically be disrupted by a number of means including, but not limited to: knockout of the responsible gene(s); suppression of expression of the responsible gene (s); disruption of required post-translational modification(s) of the product of a gene; and antagonism of an underlying mechanism of MDR, e.g. an efflux pump or enzyme.

Classes of compounds that may be discovered via the subject methods include, but are not limited to, antimicrobials, antifungals, antiseptics, disinfectants, antiproliferatives, cancer; chemotherapeutics, antagonists of prokaryotic and/or eukaryotic mechanisms of MDR, antisense oligonucleotides, analgesics, tranquilizers, and immunosuppressants.

The desirable effects of high pH on the cellular accumulation of amphipathic cations and amphipathic weakly basic compounds, and the corresponding desirable effects of low pH on the accumulation of amphipathic weakly acidic compounds, can be exploited in topical formulations, e.g. toothpastes or salves, of biologically active compounds. The compounds of these formulations may be known in the art, or may be discovered via the subject methods. In certain preferred embodiments, a amphipathic cationic disinfectant and/or a amphipathic cationic antiseptic are incorporated into a topical formulation which pH is about 9; the pH of this formulation will both reverse the pH gradient and increase the membrane potential of prokaryotes with which it comes in contact, and thereby increase the cytoplasmic accumulation of the amphipathic cationic compound(s) therein.

The effectiveness of antiseptics and disinfectants can be substantially improved according to these findings by creating conditions that favor accumulation of these antimicrobials in the target cells. The strategy takes advantage of the aforementioned changes in transmembrane pH gradient and membrane potential associated with the increase in the pH of the medium; these changes increase the rate and degree of accumulation in the cell of a wide range of substances, e.g. amphipathic weakly basic, amphipathic cationic, or amphipathic compounds. Moreover, the inactivation of multidrug resistance pumps (MDRs) acts synergistically with increased pH of the medium and increases the effectiveness of antiseptics up to 5,000 fold.

II. Definitions

The phrase "sanguinarine family of plant alkaloids" refers to the set of structurally-related amphipathic cations comprising sanguinarine, berberine, and palmatine.

As used herein, the term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental biochemical differences, including differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of rRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles prokaryotes that live at very high concentrations of salt ([NaCl]); and extreme (hyper) thermophiles (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "Eubacteria", refers to a domain of prokaryotic organisms. Bacteria include at least 11 distinct groups as follows: (1) Gram-positive (gram+) bacteria, of which there are two major subdivisions, (a) high G+C group (Actinomycetes, Mycobacteria, Micrococcus, others) and (b) low G+C group (Bacillus, Clostridia, Lactobacillus, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; (11) Thermotoga and Thermosipho thermophiles.

"Gram-negative bacteria" include cocci, nonenteric rods, and enteric rods. The genera, of Gram-negative bacteria include, for example, Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, and Fusobacterium.

The term "pathogen" is art recognized and refers generally to any organism which causes a deleterious effect on a selected host under appropriate conditions. Within the scope of this, invention the term pathogen is intended to include fungi, bacteria, nematodes, viruses, and insects.

"Gram positive bacteria" include cocci, nonsporulating rods, and sporulating rods. The genera of gram positive bacteria include, for example, Actinomyces, Bacillus, Clostridium, Corynebacterium, Erysipelothrix, Lactobacillus, Listeria, Mycobacterium, Myxococcus, Nocardia, Staphylococcus, Streptococcus, and Streptomyces.

The terms "drug resistant" or "drug resistance" as used herein to describe a property of a cell refer to the ability of the cell to withstand without cytotoxicity increased concentrations of a drug as compared to an appropriate control cell. An appropriate control cell for a cell which has been made drug resistant by continued exposure to a drug is the parental cell from which the drug resistant cell was derived. An appropriate control cell for a cell which has been made drug resistant by expression in the cell of a protein which confers drug resistance on the cell is the same cell without the protein expressed. Appropriate control cells for naturally occurring tumor cells in vivo made drug resistant by continued exposure to a drug are the same tumor cells at the time of initial exposure to the drug.

The term "biosynthetic pathway", also referred to as "metabolic pathway", refers to a set of anabolic or catabolic biochemical reactions for converting (transmuting) one chemical species into another. For instance, an antibiotic biosynthetic pathway refers to the set of biochemical reactions which convert primary metabolites to antibiotic intermediates and then to antibiotics.

The term "non-ribosomal synthesis" refers to a biosynthetic step or series of steps other than peptide bond formation in the translation of mRNAs into polypeptides. That is, the term refers to biosynthetic steps other than peptidyl transferase-catalyzed formation of peptide bonds. Likewise, "transformation of a non-proteinaceous compound" refers to the biochemical modification of a compound which is not directly produced by ribosome-mediated formation of peptide bonds.

"Ribosomal peptide synthesis", on the other hand, refers to ribosome-mediated formation of peptide bonds in the synthesis of polypeptide; though it does not include post-translational modification of the polypeptide by ribosome-independent reactions.

A "non-proteinaceous compound" refers to a compound which is not produced by ribosome-mediated formation of peptide bonds. Thus, the term includes the macrolide class of compounds and the like.

A "small molecule" refers to a compound which is not itself the product of gene transcription or translation (protein, RNA or DNA). Preferably a "small molecule" is a low molecular weight compound, e.g., less than 7500 amu, more preferably less 5000 amu and even more preferably less than 1000 amu. Examples of small molecules include, among the many compounds commonly referred to as "natural products", β-lactam antibiotics, macrolides, steroids, retinoids, polyketides, etc.

"Peptide antibiotics" are classifiable into two groups: (1) those which are synthesized by enzyme systems without the participation of the ribosomal apparatus; and (2) those which require the ribosomally-mediated translation of an mRNA to provide the precursor of the antibiotic.

The "non-ribosomal peptide" antibiotics are assembled by large, multifunctional enzymes which activate, modify, polymerize and in some cases cyclize the subunit amino acids, forming polypeptide chains. Other acids, such as aminoadipic acid, diaminobutyric acid, diaminopropionic acid, dihydroxyamino acid, isoserine, dihydroxybenzoic acid, hydroxyisovaleric acid, (4R)-4-[(E)-2-butenyl]-4,N-dimethyl-L-threonine, and ornithine can also be incorporated (Katz et al. (1977) *Bacteriological Review* 41:449–474; Kleinkauf et al. (1987) *Annual Review of Microbiology* 41:259–289). The products are not encoded by any mRNA, and ribosomes do not directly participate in their synthesis. Peptide antibiotics synthesized non-ribosomally can in turn be grouped according to their general structures into linear, cyclic, lactone, branched cyclopeptide, and depsipeptide categories (Kleinkauf et al. (1990) *European Journal of Biochemistry* 192:1–15). These different groups of antibiotics are produced by the action of modifying and cyclizing enzymes; the basic scheme of polymerization is common to them all. Non-ribosomally synthesized peptide antibiotics are produced by both bacteria and fungi, and include edeine, linear gramicidin, tyrocidine and gramicidin S from *Bacillus brevis*, mycobacillin from *Bacillus subtilis*, polymyxin from *Bacillus polymiyxa*, etamycin from *Streptomyces griseus*, echinomycin from *Streptomyces echinatus*, actinomycin from *Streptomyces clavuligerus*, enterochelin from *Escherichia coil*, gamma-(α-L-aminoadipyl)-L-cysteinyl-D-valine (ACV) from *Aspergillus nidulans*, alamethicine from *Trichoderma viride*, destruxin from *Metarhizium anisolpliae*, enniatin from *Fusarium oxysporum*, and beauvericin from *Beauveria bassiana*. Extensive functional and structural similarity exists between the prokaryotic and eukaryotic systems, suggesting a common origin for both. The activities of peptide antibiotics are similarly broad, toxic effects of different peptide antibiotics in animals, plants, bacteria, and fungi are known (Hansen (1993) *Annual Review of Microbiology* 47:535–564; Katz et al. supra; Kleinkauf et al. supra; Kolter et al. (1992) *Annual Review of Microbiology* 46:141–163).

The "aminoglycosides" and other "carbohydrate-containing" antibiotics refer to organic molecules derived at least part from a saccharide or polysaccharide. For instance, the aminoglycosides are oligosaccharides consisting of an aminocyclohexanol moiety glycosidically linked to other amino sugars. Streptomycin, one of the best studied of the group, is produced by *Streptomyces griseus*. Streptomycin, and many other aminoglycosides, inhibits protein synthesis in the target organisms.

The "ribosomally-synthesized peptide" antibiotics are characterized by the existence of a structural gene for the antibiotic itself, which encodes a precursor that is modified by specific enzymes to create the mature molecule.

The term "variegated population" refers to a population of, e.g., cells, vectors, or the like, including multiple different species. A variegated population of cells preferably includes at least $10^2$, $10^3$, $10^4$ or $10^5$ different phenotypes in the cell population. Likewise, a variegated population of vectors preferably includes at least $10^2$, $10^3$, $10^4$ or $10^5$ different vectors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "$ID_{50}$" means the dose of a drug which causes 50% of the maximum possible inhibition of a response for the given drug.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

III. Methods of the Invention

In certain embodiments, cells, under conditions wherein some or all of their endogenous MDR mechanisms are disrupted, are incorporated into assays for compounds with a desired effect on that cell line. In further embodiments, assay systems of this type will also incorporate a high pH medium to increase the cytoplasmic accumulation of amphipathic weakly basic or amphipathic cationic compounds. In certain embodiments, assay systems of this type will alternatively incorporate a low pH medium to increase the cytoplasmic accumulation of amphipathic weakly acidic compounds.

In other embodiments, cells that are recognized to be resistant may be incorporated into high pH assays that include an agent known to disrupt the MDR mechanisms expressed in that cell line. The high extracellular pH will increase the accumulation of amphipathic weakly basic or amphipathic cationic compounds in the cytoplasm of these cells; the antagonist of the operating MDR mechanisms, likewise, will also increase the accumulation of small molecules in the cytoplasm. As described in the Examples, these two effects have a synergistic interrelationship.

In further embodiments, cells that are recognized to be resistant may be incorporated into low pH assays that include an agent known to disrupt the MDR mechanisms expressed in that cell line. The low extracellular pH will increase the accumulation of amphipathic weakly acidic compounds in the cytoplasm of these cells; the antagonist of the operating MDR mechanisms, likewise, will also increase the accumulation of amphipathic weakly acidic compounds in the cytoplasm.

In additional embodiments, cells that have been genetically altered such that they no longer express the MDR phenotype may be incorporated into high pH assays of new compounds. The high extracellular pH will increase the accumulation of amphipathic weakly basic or amphipathic cationic compounds in the cytoplasm of these cells.

In further embodiments, cells that have been genetically altered such that they no longer express the MDR phenotype may be incorporated into low pH assays of new compounds. The low extracellular pH will increase the accumulation of amphipathic weakly acidic compounds in the cytoplasm of these cells.

In other embodiments, sensitive cells may be incorporated into high pH assays of new. compounds. The high extracellular pH will increase the accumulation of amphipathic weakly basic or amphipathic cationic compounds in the cytoplasm of these cells.

In further embodiments, sensitive cells may be incorporated into low pH assays of new compounds. The low extracellular pH will increase the accumulation of amphipathic weakly acidic or amphipathic anionic compounds in the cytoplasm of these cells.

The high pH assay technique may be applied without additional modifications related to the MDR phenotype; this method will allow selection of amphipathic weakly basic or amphipathic cationic compounds not currently subject to the underlying mechanism(s) of the MDR phenotype as expressed in that cell line.

The low pH assay technique may be applied without additional modifications related to the MDR phenotype; this method will allow selection of amphipathic weakly acidic or amphipathic anionic compounds not currently subject to the underlying mechanism(s) of the MDR phenotype as expressed in that cell line.

In preferred embodiments, the high pH assay technique may be applied to an MDR cell line in conjunction with a amphipathic weakly basic or amphipathic cationic cytotoxic agent known to be a substrate for MDR pumps; compounds may then be screened in this system for their ability to antagonize the MDR pumps of the MDR cell line and thereby restore to the cells of the assay sensitivity to the known cytotoxin. The compounds discovered in this approach, provided they are not cytotoxic themselves, will be chemosensitizers.

In additional preferred embodiments, the low pH assay technique may be applied to an MDR cell line in conjunction with a amphipathic weakly acidic or amphipathic anionic cytotoxic agent known to be a substrate for MDR pumps; compounds may then be screened in this system for their ability to antagonize the MDR pumps of the MDR cell line and thereby restore to the cells of the assay sensitivity to the known cytotoxin. The compounds discovered in this approach, provided they are not cytotoxic themselves will be chemosensitizers.

As detailed in the Examples, the antimicrobial potency of amphipathic compounds believed to possess weak animicrobial activity, e.g. plant alkaloids of the sanguinarine family, was significantly increased in cells whose endogenous MDR mechanisms were disrupted. This unexpected finding may lead to the discovery of novel structural classes of amphipathic antimicrobials for use in animal husbandry, aquaculture, and medicine; the use of members of these novel structural classes does not carry the threat of selecting for strains of organisms with resistance to antimicrobials currently in use in humans.

In accordance with the present invention, novel compounds are provided that target the human MDR1 gene or the human MRP gene or their transcripts which are uniquely effective in inhibiting MDR in human cancer cells. Administration of these compounds to patients having MDR cancer is done for the purpose of increasing sensitivity of the cancer(s) to the cytotoxic effects of therapeutic agents that would normally be expelled from their site of action in the tumor cells by the MRP or P-gp molecular pumps. The compounds may be used alone or in combination with certain chemical inhibitors which exhibit an inhibitory effect on the MRP or P-gp pumps. The compounds may also be used in combination with chemotherapeutic drugs to purge bone marrow or peripheral stem cell grafts of malignant cells or non-malignant mononuclear cytotoxic effector cells. The compounds may be administered to patients receiving an organ transplant, or patients with autoimmune diseases, as an immunosuppressive agent alone or with other MRP or P-gp inhibitors or with cytotoxic or cytostatic drugs.

Oligonucleotides, or analogues thereof, may be screened for their ability to reverse the multidrug resistance phenotype exhibited by cancer cells; these compounds need not be complementary to any known human gene. They may act by interfering with the function of some key molecule needed for the production of the multidrug resistance phenotype. This type of phenomenon is generally known as an "aptameric effect." The oligonucleotides or analogues exhibiting this specific aptameric effect are highly active in vitro. The degree to which these MDR-aptamers reverse the multidrug resistance phenotype is positively correlated with the degree to which, by themselves, they inhibit the in vitro proliferation of drug-resistant cancer cells. These MDR-aptamers do not have a major drug sensitizing effect on drug sensitive cells and they do not significantly inhibit the proliferation of such cells. Similarly, some MDR- and MRP-oligonucleotides or analogues exhibit both an antisense effect on MDR1 or MRP. expression and, to varying degrees, an MDR-aptameric effect. These MDR-aptamers can serve a variety of purposes, including being used: (1) to treat cancer patients, particularly those with multidrug resistant cancer, in order to sensitize the tumor to chemotherapeutic agents; (2) as probes to discover the critical molecular target in cells required for the maintenance of the multidrug resistance phenotype; and (3) as prototype MDR-aptamers in structural studies for the further development of oligonucleotides or analogues of this type for clinical use as therapeutic agents.

The methods of the invention may be used to assay for a substance that effects a multidrug resistant tumor cell. Cells from an MDR cell line may be incubated with a test substance which is suspected of effecting multidrug resistance. The effect of the substance can be determined by analyzing the drug resistance pattern of the cells and comparing the results to a control. As discussed above, a multidrug resistant cell line is resistant to anthracyclines, epipodophyllotoxins, Vinca alkaloids and other natural-product type drugs. Thus, it is possible to screen for an agonist or antagonist substance of multidrug resistance.

A method is provided for identifying a chemosensitizer of a therapeutic agent. The method involves incubating the therapeutic agent with a cell transfected with a gene which confers on the cell resistance to the therapeutic agent, both with and without a substance to be tested, determining resistance of the cell to the therapeutic agent when incubated with and without the substance to be tested and identifying a substance which is a chemosensitizer of the therapeutic agent by the ability of the substance to decrease the resistance of the cell to the therapeutic agent when incubated with the substance as compared to the resistance of the cell to the therapeutic agent when incubated without the substance. In a preferred embodiment, the gene is provided in the form of a recombinant expression vector containing a nucleic acid sequence for an MDR pump. Preferably, the cell into which the gene is transfected is drug sensitive prior to transfection so that the effects of a potential chemosensitizer are assessed in the presence of a single, isolated MDR-conferring protein. The cell used to test potential chemosensitizing substances can be a cell in culture and the therapeutic agent and substance to be tested are incubated in culture with the cell. Alternatively, the cell can be a multidrug resistant cell in a transgenic animal, and the therapeutic agent and substance to be tested are administered to the transgenic animal. Furthermore, the cell can be a cell in culture isolated from a multidrug resistant transgenic animal. The resistance of the cell for the therapeutic agent in the presence and absence of the potential therapeutic agent is assessed by determining the concentration of the therapeutic agent which is cytotoxic for the cell either in the presence or in the absence of the substance being tested.

The invention provides a method for identifying a substance which is directly cytotoxic to a multidrug resistant cell involving incubating a substance to be tested with a resistant cell line, i.e. a cell line either transfected with a gene that confers multidrug resistance on the cell or a cell line known to be resistant, and determining the cytotoxicity of the substance for the cell. Preferably, the cell into which the gene is transfected is drug sensitive prior to transfection so that the effects of a potential chemosensitizer are assessed in the presence of a single, isolated multidrug resistance-conferring protein. The cell used to test potential cytotoxic substances can be a cell in culture and the substance to be tested is incubated in culture with the cell. Alternatively, the cell can be a multidrug resistant cell in a transgenic animal and the substance to be tested is administered to the transgenic animal. Furthermore, the cell can be a cell in culture isolated from a multidrug resistant transgenic animal.

In the last several years, the frequency and spectrum of antimicrobial-resistant infections has increased in both the hospital and the community. Certain infections that are essentially untreatable are reaching epidemic proportions in both the developing world and institutional settings in the developed world. Antimicrobial resistance is manifested in increased morbidity, mortality, and health-care costs. *Staphylococcus aureus* is a major cause of nosocomial infection, especially nosocomial pneumonia, surgical wound infection, and bloodstream infection (Panlilio et al., Infect. Cont. Hosp. Epidemiol. 13: 582–586 (1992)). Other pathogens commonly associated with nosocomial infection include, but are not limited to, *Escherichia coli, Pseudomonas aeruginosa,* Enterococcus spp., Enterobacter spp., coagulase-negative staphylococci (CNS). A considerable amount of effort has been devoted to developing bacteriostatic and bactericidal agents against these and other microorganisms.

In general, the present invention provides a method for the discovery of compounds that inhibit the growth of bacterial microorganisms, such as in the treatment of Gram-positive infections, including Staphylococcus infections, Streptococcus infections, and Enterococcus infections, and in the treatment of Gram-negative infections, including Enterobacteriaceae infections, Mycobacterium infections, Neisseria infections, Pseudomonas infections, Shigella infections, Escherichia infections, Bacillus infections, Micrococcus infections, Arthrobacter infections, and Peptostreptococcus infections. For instance, the compounds discovered via the present invention might be useful in the treatment of infections caused by methicillin-resistant. strains of bacteria, e.g. methicillin-resistant strains of *Staphylococcus aureus* (MRSA; *Micrococcus pyogenes* var. *aureus*). In preferred embodiments, the present invention provides compounds that can be used to inhibit bacterial infections caused by Gram-positive bacteria, for example, *S. aureus, S. epidermidis, S. pneumonia.*

Fungicides are indispensable in agriculture to prevent plant diseases and to increase the yield of agricultural products. A number of agricultural fungicides are now used. However, some of them have poor fungicidal activities and some of them have restrictions on their use because of their toxicities in the environment. Further, when the same or similar fungicides are used for an extended period, pathogenic plant fungi which are resistant to the fungicides are generated, so that the effects of the fungicides are reduced. Thus, fungicides with sufficient fungicidal activity, which are free from the problems of environmental pollution and the emergence of drug-resistant fungi are desired.

The present invention can be applied to the discovery of compounds with fungicidal activities against a wide variety of fungi causing diseases in plants. More particularly, compounds discovered via the present invention may have fungicidal activities against, for example, rice blast (*Pyricularia oryzae*), rice sheath blight (*Rhizoctonia solani*), rice brown spot (*Cochliobolus miyabeanus*), apple powdery mildew (*Podosphaera leucotricha*), apple scab (*Venturia inaegualis*), pear scab (*Venturia nashicola*), apple blossom blight (*Sclerotinia mali*), persimmon anthracnose (*Gloeosporium kaki*), peach brown rot (*Sclerotinia cinerea*), peach scab (*Cladosporium carpophilum*), Grape gray mold (*Botrytis cinerea*), grape anthracnose (*Elsinoe amnpelina*), grape ripe rot (*Glomerella cingulata*), sugar beet cercospora leaf spot (*Cercospora beticola*), peanut brown leaf spot (*Cercospora arachidicola*), peanut leaf spot (*Cercospridium personatum*), barley powdery mildew (*Erysiphe graminis* f.sp. *hordei*), barley snow mold (*Fusarium nivale*), wheat powdery mildew (*Erysiphe graminis* f.sp. *tritici*), wheat leaf rust (*Puccinia recondita*), wheat eyespot (*Pseudocercosporella herpotrichoides*), wheat spot blotch (*Drechslera sorokiniana*), cucumber downy mildew (*Pseudoperonospora cubensis*), cucumber powdery mildew (*Sphaerotheca fuliginea*), cucumber gummy stem blight (*Mycosphaerella melonis*), cucumber gray mold (*Botrytis cinerea*), cucumber scab (*Cladosporium cucumerinum*), tomato late blight (*Phytophthora infestans*), tomato leaf mold (*Cladosporium fulvum*), tomato gray mold (*Botrytis cinerea*), strawberry powdery mildew (*Sphaerotheca humuli*), hop gray mold (*Botrytis cinerea*), tobacco powdery mildew (*Erysiphe cichoracearum*), rose black spot (*Diplocarpon rosae*), orange scab (*Elsinoe fawcetii*), orange blue mold (*Penicillium italicum*), orange common green mold (*Penicillium digitatum*) and the like.

The continuous application of fungicides over a long period of time provides phytopathogenic fungi with tolerance to them, whereby their plant disease-preventive effect is decreased. Further, fungi resistant to certain benzimidazole or thiophanate fungicides also show considerable tolerance to some other kinds of benzimidazole or thiophanate fungicides. Thus, fungi are apt to obtain cross-tolerance. Therefore, if any material decrease of their plant disease-preventive effect in certain fields is observed, their application to such fields must be discontinued. However, it is often observed that the density of drug-resistant organisms is not decreased even long after the discontinuation of the application.

IV. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2)

parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect by inhibiting an intracellular signaling pathway in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject antibacterial agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the subject compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "phannaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract or, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the antibacterial in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compositions may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular antibacterial employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject antibacterials, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The antibiotic compounds according to the invention may be formulated for administration in any convenient way for use in human or veterinary medicine, by analogy with other antibiotics.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutic effects of the first compound administered has not entirely dissipated when the subsequent compound is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

The compounds covered in this invention may be administered alone or in combination with other pharmaceutically active agents or in combination with a pharmaceutically acceptable carrier of dilutent. The compounds of the invention may be administered intravenously, intramuscularly, intraperitoneally, subcutaneously, topically, orally, or by other acceptable means. The compounds may be used to treat mammals (i.e., humans, livestock, and domestic animals), birds, lizards, and any other organism which can tolerate the compounds, and also to inhibit growth in cell culture. The compounds can also be used for effects related to their predominant activity such as for increasing the weight gain of livestock.

V. Exemplary Uses

There are a wide range of uses for the subject invention, and natural products which can be identified by the subject method. Secondary metabolites produced by microorganisms, such as fungi, reflect a wide variety of chemical structures affecting numerous biological activities in different classes of organisms, including both prokaryotes (bacteria) and eukaryotes (animals, plants, and insects). Antibiotics constitute the largest group of known bioactive secondary metabolites, acting on such diverse processes as cell wall synthesis, DNA replication, and protein synthesis. In addition to their use as antibiotics, secondary metabolites are being successfully developed and used in agriculture as pesticides, herbicides, and anti-parasitic compounds, and in treating non-infectious human diseases as inhibitors of enzyme.

To further illustrate, in animal therapies, the present method may be used to provide, e.g., angiogenesis inhibitors, insecticidal agents, antibacterial agents, antifungal agents, antiprotazoan agents, antiinflammatory drugs, antiparasitic agents, antitumor agents, cell cycle regulators, cytotoxic drugs, immune stimulants, immunosuppressants, ion channel blockers, fibrinolytic agents, free radical scavengers, prostaglandins and precursors, vasodilators, hypolipidemic agents, viral inhibitors (including reverse transcriptase and protease inhibitors), and modulators of microtubule dynamics, receptor-ligand interactions and enzyme activity (inhibitors or activators). The subject method can also provide biologically active molecules for use in agricultural applications, such as antibiotics, antifeedants, bactericides, enzymes with antibiosis activities (lysozymes, chitinases, glucanases, cellulases), fumgicides, herbicides, pesticides (e.g., antihelminthics, insecticides, acaricides, anticoccidials, antitreponemals, and antitrichomonals), ion channel blockers and promoters, miticides, nematicides, pheromones, siderophores, viricides and the like. The subject method can also yield compounds which have applications in the food industry, such as may be useful as enzymes, fatty acids, flavorings, gums, novel carbohydrates, peptides, pigments and dyes, sweeteners, and vitamins. Still other industrial applications include compounds useful in bioremediation (e.g., degradation of pesticides, toxic waste, oil, grease), as biotech enzymes (restriction enzymes, new reporter genes, antibiotic resistance markers), as industrial enzymes (amylases, proteases, lipases, phosphatases), or as new sources of polysaccharides (lubricants, thickeners). The compounds discovered via the subject method can have such activities as can be assessed using methods standard in the art (see, e.g., Franco et al. (1991) *Crit. Rev. in Biotech.* 11: 193–276, and references therein). The subject method, therefore, can further involve the use of, inter alia, biochemical assays, cell or tissue culture assays, and animal model systems. Several exemplary embodiments of these assays are described below.

Antibiotic and Antiviral Activities

In one aspect, the methods of the present invention can be used to discover compounds which display some antibiotic activity, e.g., antibacterial, antifungal and/or antiviral.

Historically, discovery of antibiotics occurred through evaluation of fermentation broths for anti-bacterial or antifungal activity. For instance, many proteobacteria produce β-lactam antibiotics. This has been documented in Chromobacterium, Pseudomonas, Agrobacterium, Serratia, and Erwinia (de Lorenzo et al. (1984) *TIBS* 9: 266). Additionally, production of metabolites having antifungal activity, such as phenazines and phloroglucinols, have been documented in Pseudomonas (see, for example, Buysens et al. (1996) *Appl. Environ. Microbiol.* 62:865–871). Myxobacteria have emerged as major producers of novel biologically active compounds (Reichenbach et al., 1993, In *Third International Conference on the Biotechnology of Microbial Products: Novel Pharmacological and Aprobiolopical Activities. Developments in Industrial Microbiology Series* Volume 33. V. P. Gullo, J. C. Hunter-Cevera, R. Cooper, and R. K. Johnson, Eds. Society for Industrial Microbiology).

Anti-bacterial activities can be identified using a number of standard assays known in the art. For example, a culture of bacteria, such as a bacterial lawn, can be contacted with a compound, e.g., filter paper discs doped with the extract, and the areas of lysis characterized. In other embodiments, the compounds are added to a liquid culture of a target organism, and the inhibition of bacterial cell growth can be determined, e.g., by turbidimetric readings. In addition to detecting general effects on bacterial growth and viability, the screening methods of the invention can involve assays for effects on bacteria-specific structures, enzymes, or processes.

A large number of antifungal compounds have been identified using classic approaches, e.g., evaluating samples in primary tests directly against a range of filamentous fungi and yeasts, e.g., *Candida albicans*, grown in agar plates, or in some cases, directly against phytopathogenic infestations (Bastide et al. (1986) *Mircen J. Appl. Microbiol. Biotechnol.* 2:453; and Haruo, (1987) *Gendai Kagaku Zokan* 9:16). Such asssays can be readily adapted for use in a detection step of the subject method. Several examples of fungi-specific targets include chitin and glucan synthases (Selitrennikoff et al., (1983) *Antimicrob. Agents Chemother.* 23:757; Kirsch et al., (1986) *J. Antibiot.* 39:1620; and Denisot et al., (1990) *9th Int. Symp. Future Trends in Chemother.*, Geneva, March 26 to 28, page 47), and cutinases (Koller et al., (1990) *J. Antibiot.* 43:734; Umezawa et al. (1980) *J. Antibiot.* 33:1594).

To further illustrate, compounds which modulate sterol biosynthesis have valuable pharmacological properties. In particular, they can have a pronounced antifungal activity, e.g., such as ketoconazole and terbinafine. These compounds can accordingly be used as medicaments, especially for the control or prevention of topical or systemic infections which are caused by pathogenic fungi in mammals.

Ergosterol is the principal membrane sterol of fungi. It is structurally similar to its animal counterpart, cholesterol, except that ergosterol has a methyl group and two double bonds not present in cholesterol. In yeast, ergosterol affects membrane fluidity and permeability and plays an essential role in the yeast cell cycle. Yeast cells can take up cholesterol and decrease their requirement for ergosterol to very low levels, but cholesterol alone cannot completely substitute for ergosterol (Gaber et al. (1989) *Mol. Cell. Biol.* 9:3447–3456). Though the biosynthesis of ergosterol in fungi involves steps distinct from cholesterol biosynthesis in animals, sterol biosynthesis in different organisms shares many common steps. At least one cytochrome P450 is implicated in sterol biosynthesis. The term "cytochrome P450" is a trivial name for a class of cytochromes that includes a number of heme proteins exhibiting a characteristic absorption maximum at 450 nm when combined with CO in the reduced state ('P' denotes pigment; hence, the name). These cytochromes occur in most animal tissues, plants and microorganisms and catalyze the monooxygenation of a wide variety of amphipathic substances, including lipophilic endogenous compounds and xenobiotics; these enzymes serve as oxygenating catalysts in the presence of one or more electron transfer proteins or redox enzymes.

In certain embodiments, compounds are screened as sterol biosynthesis inhibitors that may be of potential use as fungicides or antihypercholesterolemic agents via the induction of lanosterol 14-α-demethylase, an enzyme in the biosynthetic pathway of ergosterol and cholesterol. Compounds that inhibit ergosterol biosynthesis in this system induce lanosterol 14-α-demethylase activity in the culture. In one screening test, compounds are incubated in a culture of a *Saccharomyces cerevisiae* strain sensitive to ergosterol biosynthesis and containing a gene fusion of a lanosterol 14-α-demethylase clone with a gene for bacterial β-galactosidase. After incubation of the culture, an increase in lanc sterol 14-α-demethylase activity is determined indirectly by measuring β-galactosidase activity. The culture media contains a chromogenic substrate of β-galactosidase such as ortho-nitrophenyl-β-D-galactopyranoside or 5-bromo-4-chloro-3-indoyl-β-D-galactopyranoside, so that active samples are identified by the production of a visibly colored product. For comparison purposes, screening tests may employ a lanosterol 14-α-demethylase inhibitor such as dinaconazole as a positive control.

Anti-viral compounds can be identified by screening for inhibitors of virus-specific enzymes, such as retroviral reverse transcriptases. Other virus-specific processes, such as viral uncoating, viral receptor binding, and cell fusion (e.g., syncytium formation caused by HIV) can also be targeted in the screening methods of the invention.

The antiviral properties of the compounds may be determined in an assay which exploits the unique properties of the virus. For instance, the influenza virus is a negative strand virus with a segmented genome. The synthesis of viral mRNA is accomplished by a virally-encoded transcription complex. Influenza virus is unique in that it requires capped and methylated palmers which are obtained from host cell RNA polymerase H transcripts to initiate mRNA synthesis. An in vitro influenza transcription assay was established to detect agents that are capable of inhibiting the transcription apparatus of the influenza virus.

U.S. Pat. No. 5,624,928 describes an exemplary assay for detecting inhibitors of the transcription apparatus of the influenza virus which are required to initiate viral mRNA (messenger RNA) synthesis. Briefly, to each well of a 96-well microtiter plate is added a stock mix of the virus, the test extract or compound, labeled nucleotides, and water. Ten microliters of primer (alfalfa mosaic virus (ALMV) RNA at 0.015 mu g/ml) is also added to the wells. The plates are gently mixed on a shaker for 30 seconds and then incubated for 60 minutes in a 31° C. water bath. At the end of this period, the plates are removed from the water bath, placed on a bed of ice and the reaction stopped with (i) sterile saturated sodium pyrophosphate solution containing 0.5 mg/ml RNase-free tRNA and (ii) ice-cold 40% TCA, and the plates allowed to stand on ice for 15 minutes. The samples are then collected, using a cell harvester, washed twice with 5% TCA, then twice with 95% ethanol and then transferred to sealing bags. The incorporation of the labeled nucleotides into a reverse transcript of the ALMV RNA is detected.

Anti-Tumor Activities

To identify anti-tumor activities, cultured tumor cell lines or cultured tumors can be contacted with compounds and their effects on cell growth and viability monitored. Another approach involves screening for compounds that induce differentiation of tumor cells, e.g., that cause these cells to lose their tumorigenicity (Franco et al., (1991) *Crit. Rev. in Biotech.* 11: 193–276). An in vitro disease-oriented screening program can utilize a large panel of human tumor cell lines grown initially in vitro and assessed for cytotoxicity by the MTT assay (Carmichael et al. (1987) *Cancer Res* 47:936–42) and subsequently the sulforhodamine B protein assay (Skehan et al. (1991) *Eur J Cancer* 27:1162–8). The aim of this screen is to select compounds exhibiting selective activity against distinct histological tumor types.

Enzymes can also be used as targets for identifying anti-tumor activities. Enzymes that have been successfully employed as targets in the search for anti-tumor agents include protein tyrosine kinases, which are components of signal transduction pathways regulated by a number of oncogenes, phosphatidylinositol kinase, spermidine synthase, and topoisomerases. As the differences between tumor and non-tumor cells become more apparent, tumor cell-specific targets can be used in the screens in order to identify extracts or compounds that are not toxic to the patient.

Compounds that exhibit anti-tumor activities in biochemical and cell culture assays can be tested further in appropriate animal model systems.

Immunosuppressive Activities

Immunosuppressive activities can be identified using a number of standard methods in the art, including the mixed lymphocyte reaction, which measures lymphocyte proliferation (Goto et al., (1982) *J. Antibiot.* 35:1286), and screens for macrophage activation (Tanida et al. (1989) *J. Antibiot.* 42:1619). Inhibitors of T cell activation can be identified by growing cultured T cells in the presence of the candidate extract or compound, crosslinking with activating agents, such as antibodies to CD3 and CD4 surface molecules and a secondary antibody, which normally activate T cells, and determining the level of T cell activation. T cell activation can be quantified by, e.g., a bioassay in which IL-2 production is measured by applying the T cell culture supernatant to CTLL-20 cells, which require IL-2 to live (Sleckman et al., (1987) *Nature* 328:351).

The cellular immune response involves a very complex set of interactions between antigens, T cells, B cells, macrophages, and numerous factors, such as cytokines, which are released by the cells during the course of the interactions. In one embodiment, compounds can be tested for their effect on T cell activation. While specificity of the T cell response is determined by antigen-specific binding to the T cell antigen receptor (TCR), binding to at least one secondary receptor is also necessary for activation. One such secondary receptor is CD28 which, upon stimulation, induces the activity of nuclear proteins which can increase the production of interleukin-2 and possibly other cytokines by binding to an enhancer region associated with the cytokine genes. Immunosuppressive drugs which act by suppression of the CD28 pathway may have a number of advantages over drugs which act through other mechanisms. Thus, according to the present invention, screening assays for immunosuppressive compositions can comprise exposing cultured T cells to a compound, where the T cells produce an observable signal as a result of normal CD28 stimulation. The T cells are cultured under conditions which will, in the absence of effective CD28 stimulation, produce the observable signal, generally requiring the presence of substances which result in stimulation of both CD28 and the T cell receptor (TCR). The assay can thus identify compounds that at least partially suppress the stimulation of CD28, thus resulting in a decrease in the observable signal.

T cells used in the screening assays of the present invention can be obtained from T cell lines which have been modified to incorporate a CD28 enhancer region in a reading frame with a reporter gene so that exposure of the cells to conditions selected to induce the CD28 receptor will result in expression of the reporter gene. The T cell lines may be derived by modifying previously established human or mouse T cell lines and hybridomas, where the starting cell lines and hybridomas are capable of expressing certain cytokine gene(s), as discussed below.

The CD28 enhancer region may be derived from the 5' flanking region of a cytokine gene, where the cytokine gene selected should be one which is normally expressed in the cell line being modified. The enhancer region will include at least that portion of the 5' flanking region which is bound by the CD28 nuclear protein which is produced as a result of stimulation of the CD28 receptor, as described below. Suitable enhancer regions may be obtained from such genes as the IL-2 gene, the GM-CSF gene, the IL-3 gene, the G-CSF gene, or the γ-IFN gene.

Compounds discovered via the methods of the present invention found to possess immunosuppressive activity in the cell culture assays can be further tested in animal model systems. A candidate compound, or a purified or semi-purified fraction thereof, is administered to an immunocompetent animal, for example, a mouse which has a non-MHC matched skin graft, and the effect of the compound on, e.g., T cell or macrophage activation is determined by monitoring the immune response of the mouse.

As mentioned above, preferable screening assays are designed to identify biological activities directed specifically against the target cell, e.g., an infectious pathogen or a tumor cell, and not cells of the host organism, in order to decrease the likelihood of toxicity problems. Especially in cases where the potential therapeutic biological activity is directed against a process or structure which may be similar in the target cell and the host, it is critical to determine the relationship between the effectiveness and the toxicity of the treatment. This can be determined by standard methods using both cell culture assays and animal model systems (*The Pharmacological Basis of Therapeutics,* Goodman and Gilman, Eds. MacMillan Publishing, New York, 1980, pp. 28–39, and 1602–1614).

Lipid Biosynthesis

The subject method can also be used to identify compounds that effect lipid biosynthesis. To illustrate, surface-exposed unusual lipids containing phthiocerol and phenolphthiocerol are found only in the cell wall of slow-growing pathogenic mycobacteria and are thought to play important roles in host-pathogen interaction. The enzymology and molecular genetics of biosynthesis of phthiocerol and phenolphthiocerol are unknown; though it has been postulated that a set of multifunctional enzymes are involved in their synthesis, and that these genes are clustered on the bacterial genome (Azad et al. (1997) *J Biol Chem* 272: 16741–5).

Modulators of Extracellular Factors

In one embodiment, the compounds can be assayed for their ability to alter the bioactivity of an extracellular protein, lipid, carbohydrate or the like. For instance, compounds may be sought that inhibit the action of blood coagulation factors, thrombolytic factors, or enzymes aberrantly upregulated in diseases states, such as superoxide dismutase or the like.

Modulators of Intracellular Signaling

Still another class of molecules which can be obtained and identified in the method of the present invention are those which modulate intracellular signalling, e.g., by inhibiting or potentiating protein-protein (intermolecular or intramolecular interactions), protein-DNA, protein-lipid or protein-2nd messenger interactions, inhibiting or potentiating intracellular enzymes, or inhibiting or potentiating ion channel passivity, and the like. As described above, compounds can be sampled with purified or semi-purified components, lysates, whole cells or any other convenient way of contacting the products of the invention with the intended target in a manner which permits generation of a detectable signal. That signal may be, for instance, a change in the a cell's phenotype, rate of proliferation or survival, transcription of a reporter gene, changes in $2^{nd}$ messenger levels, a change in an enzyme's activity towards a detectable substrate (or one which produces a detectable product), a change in the amount or characteristics of protein complexes or the localization of a protein, e.g., within various cellular compartments. To further illustrate, the detection step of the instant assays can be derived to identify extracts or compounds of the subject invention that, for illustration, modulate a protein kinase (e.g., serine/threonine kinase, tyrosine kinase), a protein phosphatase (e.g., serine/theronine phosphatase, tyrosine phosphatase), interactions mediated by SH2 domains (e.g., with phosphotyrosine residues), interactions mediated by SH3 domains, interactions mediated by leucine zipper domains, phosphatidyl inositol kinases, adenyl cyclases, interactions involving G proteins (e.g., with a G protein coupled receptor, between the α subunit with β/γ dimer, or downstream signal transduction proteins), phospholipases, phosphodiesterases, interactions between DNA binding proteins and DNA, and ion flux through ion channels. The interactions can occur between components of the same cell compartment, as between two intracellular proteins, or different compartments, such as between a cell surface receptor and an intracellular signal transduction protein.

Identification of Compounds Responsible for the Biological Activities

The biological activity can be further characterized by determining the structure of a compound responsible for the activity using stanjrpethods, such as liquid-liquid, liquid-solid, or affinity chromatography with normal phase, reverse-phase, ion-exchange, and gel filtration techniques being implemented as needed (Box, (1991) in *Discovery and Isolation of Microbial Products*, Verall, M. S., Ed., Ellis Horwood, Chichester, 1985; Franco et al. (1991) *Crit. Rev. in Biotech.* 11:193–276). The purification process can be monitored by co-fractionation of the biological activity, using any of the screening assays described above. Once purified, the structure of the compound can be determined using standard methods, including nuclear magnetic resonance spectroscopy, mass spectrometry, and X-ray crystallography.

VI. Exemplification

The invention now being generally described, it will be more readily understood by reference to the following examples which are included merely for purposes of illustration of certain aspects and embodiments of the present invention, and are not intended to limit the invention.

EXAMPLE 1

Microorganisms express multidrug resistance pumps (MDRs) that can confound antibiotic discovery. We propose the use of mutants deficient in MDRs to overcome this problem. Sensitivity to quinolones and to amphipathic cations (benzalkonium chloride, cetrimide, pentamidine, etc.) was increased 5 to 30-fold in a *Staphylococcus aureus* mutant with a disrupted chromosomal copy of the NorA MDR. NorA was required both for increased sensitivity to drugs in the presence of an MDR inhibitor and for increased rate of cation efflux. This suggests that NorA is the major MDR protecting *S. aureus* from the antimicrobials studied. A 15 to 60-fold increase in sensitivity was also observed in wild type cells at an alkaline pH that favors accumulation of cations. This effect was synergistic with a norA mutation, resulting in an increase up to 1,000-fold in sensitivity to a number of antimicrobials. The usefulness of applying MDR mutants for natural product screening was further demonstrated by increased sensitivity of the norA$^-$ strain to plant alkaloid antimicrobials.

Introduction

Inhibition of target cell growth is a traditional approach for screening natural antimicrobials. This method has yielded all of the natural antibiotics currently in use. New antibiotics are continued to be discovered at a rate of >500/year (1) but these almost invariably belong to previously identified classes of compounds, making it likely that pathogens will be able to rapidly build up resistance to these "new" drugs. The increasing threat of drug resistant pathogens is causing a renewed interest in the discovery of novel antibiotics. A current trend is to identify essential genes/proteins that are not targets for known antibiotics (e.g., the bacterial cell division protein FtsZ) and use the purified proteins to search for potent binding ligands from natural sources or combinatorial libraries (2).

A different strategy is to use traditional broad-based whole cell screening, but increase the probability of finding new antibiotics by gathering producing organisms from untapped environments, such as the ocean (1). A general problem facing both in vitro and whole-cell screening is that the ambient concentration of potential drugs is prone to be low. The problem with screening using whole cells is further exacerbated by numerous multidrug pumps found in all bacteria and yeast studied so far (3–6). In *E. coli*, for example, there are at least 10 MDRs with overlapping specificities that can protect against most antibiotics, both natural and synthetic (3,4). During therapy, antibiotics are routinely administered at high concentrations that are usually sufficient to overcome the action of MDR pumps. However, extrusion of antibiotics present at low concentrations in the process of screening will inevitably diminish the chances of discovery. The use of MDR$^-$ mutants has the potential for improving the sensitivity of antimicrobial discovery.

*Staphylococcus aureus* is an important human pathogen, and many antibiotic resistant strains have been isolated (7). The NorA MDR pump of *S. aureus* protects the cells from norfloxacin and a number of amphipathic cations, such as the common disinfectants benzalkonium chloride and cetrimide (8,9). We find that a mutant of *S. aureus* with a knockout in the norA gene coding for the MDR pump has a substantially increased sensitivity to a large number of antimicrobials, including therapeutically significant compounds. We also find that increasing the pH of the medium that favors accumulation of basic substances in the cell acts synergistically with the norA$^-$ mutation, leading to an increase in sensitivity of up to 1,000-fold. This approach may offer a significantly higher sensitivity of drug detection as compared to standard in vitro screening.

Materials and Methods

Disruption of the norA gene. Chloramphenicol acetyltransferase (CAT) gene was isolated by digesting plasmid pLI50 (10) with Sau3A (New England Biolabs). The CAT gene was cloned into the BamHI site of plasmid pSP72 (Promega) to yield plasmid PCH22. Chromosomal DNA from *S. aureus* RN4220 was isolated according to the protocol of Qiagen, Inc. Part of the 1050 bp norA gene lacking a 80 bp N-terminus and a 20 bp C-terminus was PCR-amplified from chromosomal DNA using primer A:5'-GCTCTATGTTGC-TTTTCAATT and primer B:5'-CTGTTTATTTAAAAGATTTGGG. This fragment was cloned into the EcoRI/EcoRV site of PCH22 to yield plasmid PCH23. *S. aureus* were transformed by PCH23 using electroporation (11). Cells were plated on trypticase soy agar (TSA) with chloramphenicol. A transformant colony was picked after 24 hours of incubation at 37 C., regrown, plated on CAM medium and a large colony was picked for further work. Primer P31 (5'-AACGTCATCACATGCACCAA) and primer PT7 (5'-TAATA-CGACTCACTATAGGG) (FIG. 1) were used for PCR amplification to examine the disruption of the norA gene.

Efflux of Ethidium Bromide. EtBr has high fluorescence when bound to DNA, making it possible to measure efflux from the cell. Freshly cultured cells (1 ml, $OD_{600}$=4) were pelleted and washed twice with 20 mM HEPES/NaOH (pH 7.0) buffer. Cells were then resuspended in 1 ml of HEPES buffer containing 10 mM CCCP and 10 mg ethidium bromide followed by incubation at 37 C. for 30 min (24). The cells were centrifuged, washed and resuspended in ice-cold 30 mM HEPES buffer. Fluorescence was measured with a Perkin-Elmer LS-5B luminescence spectrometer at 530 nm excitation, 600 nm emission wavelengths.

Determination of minimal inhibitory concentrations (MICs). MICs were determined by serial two-fold dilution of antimicrobials in Mueller-Hinton broth containing chloramphenicol (34 mg/ml). Most antimicrobials were from Sigma, and ciprofloxacin was from Bayer Co., West Haven, Conn. Around $10^5$ cells were inoculated in 1 ml of medium for the test. MICs were read after 18 hours of incubation at 37 C. with aeration. The 50% inhibitory concentration ($IC_{50}$) was determined by growing cells in microtiter plate wells and reading the optical density after overnight growth at 650 nm.

Results

Antimicrobial properties of the norA mutant. Disruption of the chromosomal copy of the norA gene was performed by replacement with a norA sequence interrupted by a CAT cassette (see Materials and Methods). The disrupted chromosomal sequence was analyzed by PCR using a primer immediately outside of the norA gene and a primer specific for the disrupted sequence. A PCR product of the predicted size (1.5 kb) and composition was obtained from the norA$^-$; but not from the wild type strain, confirming that the chromosomal copy of norA was disrupted.

Table 1 shows the susceptibility of the norA mutant towards a range of antimicrobials. Using either MIC or $IC_{50}$ to calculate the sensitivity of the norA$^-$ strain relative to the wild type gave similar results. Increased resistance to norfloxacin and amphipathic cations of strains overproducing NorA was previously described (9), and a recent study reported increased sensitivity of norA$^-$ to quinolones (13). Our data show that amphipathic cations are generally better substrates of the pump than are quinolones. Many other tested antimicrobials do not appear to be substrates of the pump (Table 1).

Testing for additional MDRs in *S. aureus*. We wished to know if additional MDR pumps took part in the quinolone and amphipathic cation resistance. Identifying and disrupting these additional MDRs would further improve the sensitivity of the strain and would be useful for drug discovery. A simple way to check the presence of MDR activity is to employ an MDR inhibitor. Reserpine is a broad range MDR inhibitor that acts upon diverse MDRs from NorA (major facilitator family of translocases powered by the proton gradient) to human P-glycoprotein (belonging to the ABC family of ATP-dependent translocases) (14). Addition of reserpine increased the sensitivity of the wild type to drugs in accordance with prior observations (8), but had virtually no effect on the norA mutant. The mutant strain was consistently more sensitive than the wild type treated with reserpine, suggesting that inhibition by reserpine was incomplete. The important and rather unexpected conclusion from this experiment in that NorA is the principal *S. aureus* MDR pump, responsible for the resistance to the chemically diverse compounds we tested.

To examine this more directly, efflux of ethidium bromide (EtBr) from wild type and norA$^-$ cells was measured. Cells were deenergized with an uncoupler, loaded with EtBr, washed and diluted into a buffer medium. The rate of EtBr efflux was significantly greater in the wild type in the presence of a respiratory substrate as compared to the norA$^-$ mutant. The basal level of EtBr leakage from deenergized wild type cells was comparable to EtBr efflux from energized norA$^-$ cells. This suggests that NorA is indeed the primary route for energy-dependent EtBr efflux.

Synergy between a norA mutation and alkaline pH. It seemed possible to further increase the sensitivity towards amphipathic cations by increasing the pH of the medium. Amphipathic cations, including the ones we tested, come in two major groups—strong cations like quaternary ammonium compounds and imino-substances; and weak bases such as pentamidine or chlorhexidine. The cytoplasmic pH of the bacterial cell is maintained near 7.5 when the external pH is in the range of 5 to 9 (12). At alkaline pH, an electrogenic $Na^+/nH^+$-antiporter leads to the acidification (relative to the external medium) of the cytoplasm in order to maintain the pH homeostasis (12). Hence, at pH 9, the pH gradient across the membrane is inverted. When the pH gradient is inverted, there is a concomitant compensatory increase in the membrane potential (12). The elevated membrane potential will lead to an increased accumulation of such permeant cations as TPP and quaternary ammonium compounds. The inverted pH gradient will also act to increase the accumulation of weak bases. The permeant form is the unprotonated species (13), and with a typical pK of 9 for an amino group this means that increasing pH from 7 to 9 will increase the concentration of the permeant species 50-fold.

At pH 9, *S. aureus* grew at approximately 70% of the growth rate at pH 7.2 (not shown). The sensitivity to all amphipathic cations increased significantly at pH 9 (Table 2). For example, sensitivity to pentamidine increased approximately 30-fold at pH 9 in the wild type. The NorA pump is electrogenic (17) and continues to protect the cell at alkaline pH. A norA mutation also leads to a 30-fold increase in the sensitivity to pentamidine. When combined, pH 9 and the norA mutation provided a strong synergistic effect, increasing sensitivity by an impressive 1,000-fold. This decreased the MIC for pentamidine to 10 ng/ml.

Among the substances we tested for antimicrobial activity were two plant alkaloids, berberine and palmatine which are strong amphipathic cations resembling quaternary ammonium compounds. Based on comparison of MIC from wild type and norA$^-$, both appear to be substrates of NorA; sensitivity to both of them was further increased at pH 9. This observation validates the idea of using MDR mutants and high pH media for discovery of natural antimicrobials.

Discussion

Disruption of the norA gene coding for a pmf-dependent MDR pump increased the sensitivity of *S. aureus* 5 to 30-fold to NorA substrates, primarily amphipathic cations. Reserpin, a general inhibitor of MDRs, failed to further increase sensitivity of norA⁻ cells to these antimicrobials. The rate of efflux of EtBr in deenergized wild type cells was the same as efflux from energized norA⁻ cells. Taken together, these observations strongly suggest that NorA is the major multidrug pump responsible for efflux of amphipathic cations from *S. aureus*. These substances are also good substrates for a majority of other MDR pumps from gram-positive organisms. In gram-negative bacteria, the known repertoire of MDR pumps includes neutral compounds (the EmrAB pump (18)) as well as amphipathic cations and anions (the AcrAB pump (19)). Experimental data and DNA analysis from whole genome sequencing projects suggest that several different MDRs are present in a given microbial species. This number varies from a putative high of 25 in the yeast *S. cerevisiae* to a low of four in the parasite *H. influenzae* (4). It is noteworthy that *H. influenzae* has a "bare-bones" genome two times smaller than that of *E. coli* and does not have a complete Krebs cycle (20), yet has four different MDR pumps that seem to be essential. Without access to the complete *S. aureus* genomic sequence it is hard to tell if NorA is the only MDR pump. There may be additional MDRs that require specific inducers, for example. The *B. subtilis* MDR pump BMR (21) and the EmrAB pump of *E. coli* (22) are induced by their substrates. At the same time, two other *B. subtilis* MDRs BLT (23) and BMRIII (24) are not expressed under normal growth conditions or in the presence of known MDR substrates.

It is interesting to note that the favored substrates of many MDR pumps, including NorA, are amphipathic cations, yet few natural antimicrobials of this type are known. It is not surprising that weak bases are rarely antimicrobial since these compounds will be excluded from the cell by the pH gradient when the external pH is <7.5. Discovered initially as weak antimicrobials, many of these compounds (doxorubicin, mytomicin) are now used as antineoplastic agents. Strong amphipathic cations, on the other hand, will accumulate in the cell in accordance with the membrane potential and would be expected to be found as antibiotics more frequently. Yet the only currently known examples come from a small group of plant alkaloids. Perhaps it is precisely the ubiquity of MDR pumps among the test strains that is responsible for the underdetection of these compounds in the process of drug discovery. Once identified, these new antimicrobials could be effectively deployed either in combination with an MDR inhibitor or simply at a concentration sufficiently high to overcome the pump.

We took advantage of the accumulation of amphipathic cations in the cell at high pH to further increase cell sensitivity to these antimicrobials. A norA mutation and high pH acted synergistically and increased the sensitivity to pentamidine, for example, 1,000-fold.

Our findings of an MDR⁻/high pH synergy will be useful for the discovery of amphipathic cationic antimicrobials. It seems that sensitivity of an antimicrobial screen could be further increased with the use of alkiliphilic bacteria that can grow at pH 10.5 and maintain a high inverted pH gradient (21). A somewhat similar strategy can be used in the discovery of weak acids that accumulate in the cell using the pH gradient. Weak acid antimicrobials have been used in food preservation (salicylate, benzoate) and as antineoplastic agents (mycophenolic acid, nogalamycin). Decreasing the pH of the medium and employing acidophilic bacteria in combination with MDR mutations or MDR inhibitors should significantly increase the sensitivity of discovery of these compounds as well.

TABLE 1

NorA Dependence of Antimicrobial Resistance as Measured by MIC.

| Drugs | RN 4222 (WT) MIC (μg/ml) | | KLE 820 (norA-) | | Sensitivity[c] |
|---|---|---|---|---|---|
| | −R[b] | +R[b] | −R | +R | |
| EtBr[a] | 5 | 1.25 | 0.33 | 0.33 | 16 |
| TPP | 15.6 | 7.8 | 1.9 | 1.9 | 8 |
| Acriflavine | 20 | 10 | 2.5 | 2.5 | 8 |
| Norfloxacin | 1.25 | 0.67 | 0.33 | 0.33 | 4 |
| Ciprofloxacin | 0.67 | 0.33 | 0.16 | 0.16 | 4 |
| Kanamycin | 0.33 | N.D. | 0.33 | N.D. | 1 |
| Erythromycin | 0.195 | N.D. | 0.195 | N.D. | 1 |
| Gentamycin | 0.62 | N.D. | 0.62 | N.D. | 1 |
| Tetracycline | 0.097 | N.D. | 0.097 | N.D. | 1 |
| Cephalothin | 0.15 | N.D. | 0.15 | N.D. | 1 |
| Lincomycin | 0.6 | N.D. | 0.6 | N.D. | 1 |
| Vancomycin | 1.5 | N.D. | 1.5 | N.D. | 1 |
| Clindamycin | 0.047 | N.D. | 0.047 | N.D. | 1 |

[a]TPP, tetraphenylphosphonium bromide; EtBr, ethidium bromide.
[b]−R, no reserpine; +R, 20 μg/mL reserpine; N.D., not determined.
[c]Sensitivity of norA- as compared to the wild type in the absence of reserpine.

TABLE 2

Synergistic effect of high pH and a norA mutation.

| Drugs | RN 4222 (WT) MIC (μg/mL) | | KLE 820 (norA-) | | Sensitivity norA- at pH 9 vs. WT at pH 7.2 |
|---|---|---|---|---|---|
| | pH 7.2 | pH 9 | pH 7.2 | pH 9 | |
| Pentamidine | 10 | 0.3125 | 0.3125 | 0.0097 | 1030 |
| EtBr | 5 | 0.078 | 0.3125 | 0.01 | 500 |
| Berberine | 60 | 3.75 | 7.5 | 0.23 | 260 |
| Palmatine | 200 | 12.5 | 50 | 0.78 | 256 |
| TPP | 15.6 | 0.48 | 1.98 | 0.12 | 130 |
| Betizalkonium Chloride | 0.67 | 0.08 | 0.16 | 0.0104 | 64 |
| Chlorhexidine | 0.5 | 0.06 | 0.125 | 0.0156 | 32 |
| Puromycin | 20 | 2.5 | 20 | 2.5 | 8 |
| Norfloxacin | 1.25 | 1.25 | 0.33 | 0.33 | 4 |

EXAMPLE 2

An Approach to Improve the Efficiency of Antiseptics and Disinfectants

The effectiveness of antiseptics and disinfectants can be substantially improved according to our findings by creating conditions that favor accumulation of these antimicrobials in the target cells. The rationale is to take advantage of changes in transmembrane pH gradient and the membrane potential that increase the rate and degree of accumulation in the cell of a wide range of substances. We find that inactivation of multidrug resistance pumps (MDRs) acts synergistically with changes of pH and increases the effectiveness of antiseptics up to 5,000 fold.

1. Cationic Disinfectants/Antiseptics

Increasing the pH of the growth medium to 9 leads to an increase in the membrane potential that could lead to a stronger accumulation and thus more effective antimicrobial action of cationic antimicrobials. In the case of weak bases, at pH 9 the pH gradient inverts, the concentration of the neutral basic species that permeates into the cell increases, and the protonated base accumulates inside the cell driven by the pH gradient. A large variety of common antiseptics and disinfectants belong to these two types of compounds. The concept of increasing the potency of cationic and basic antimicrobials at high pH was tested with a number of compounds such as chlorhexidine, pentamidine, benzalkonium chloride and others against S. aureus (Table 1). A change of pH from 7 to 9 significantly increased the effectiveness of these antimicrobials.

Cationic and basic compounds are good substrates of MDR pumps, and the use of a S. aureus mutant with a disruption in the NorA MDR showed that this strain is substantially more sensitive to disinfectants and antiseptics than the wild type (Table 1).

The two factors—high pH and disruption of an MDR pump—had a synergistic effect (Table 1). For example, a pH increase caused a 33-fold increase in sensitivity to pentamidine, and a NorA disruption also produced a 33-fold increase in sensitivity. When combined, the increase in pentamidine potency was 1,000-fold. This suggests that using an MDR inhibitor instead of an MDR mutation in combination with high pH should strongly increase the potency of basic and cationic antimicrobials.

Experiments with the known MDR inhibitor reserpine show that the inhibitor can substitute for an MDR mutation (Table 2).

A small molecule MDR inhibitor (I), which is substantially more active than reserpine, was tested alone and in combination with high pH as a potentiator of antiseptics and disinfectants. At pH 7, I (10 $\mu$g/mL) had a stronger potentiating effect than reserpine or a norA mutation in a number of cases (Table 3). It appears that I inhibits additional MDR pump(s).

These results suggest a combination of high pH and an MDR inhibitor might be of significant value. In these experiments, for example, there was a 133-fold potentiation of the action of chlorhexidine. This antiseptic is apparently the only agent that effectively fights plaque. Its use has been limited because at concentrations currently employed it can cause blackening of teeth. The prospect of decreasing by 100-fold the concentration of chlorhexidine required for activity with a combination of an MDR inhibitor and high pH is very promising. The pH of a toothpaste or a mouthwash can be increased by simply adding baking soda (Arm & Hammer, a conventional baking soda toothpaste, has a pH of 8.7 according to our measurements). Another possibility for effective use of an antiseptic at high pH with a combination of an MDR inhibitor is in a douche with baking soda (Beecham) that has a pH of 9.

2. Plant Alkaloids

We found that cationic plant antimicrobial alkaloids such as palmatine, berberine and sanguinarine are good substrates of MDR pumps. This fact would account for the weakness of these compounds as antimicrobials. For example, berberine has an MIC of 60 $\mu$g/mL against S. aureus, but a norA mutation increases its potency 32-fold (Table 1). An increase in pH has a synergistic effect, resulting in a 260-fold increase in the potency of berberine, decreasing its MIC to 0.23 $\mu$g/mL.

The proprietary MDR inhibitor mentioned above had a strong potentiating effect on berberine, increasing its potency 150-fold (Table 3). High pH further increased the potency of berberine, decreasing its MIC to 12 ng/mL. This combination of high pHl and an MDR inhibitor will make berberine a very good candidate for inclusion in oral care products (the substance has been used orally in traditional medicine and in eye drops in the US and has low toxicity). Palmatine would be another possible alkaloid antiseptic to explore using this technology.

Sanguinarine, another alkaloid of this class, has been used as an antiseptic in toothpaste (Viadent) with mixed results. The proprietary MDR inhibitor and high pH cumulatively increase the potency of sanguinarine approximately 100-fold. Application of this technology might dramatically improve the effectiveness of the existing sanguinarine-based products.

TABLE 1

Synergistic effect of high pH and a norA mutation.

| Drugs | RN4222 (WT) MIC ($\mu$g/mL) | | KLE 820 (norA$^-$) MIC ($\mu$g/mL) | | Sensitivity norA$^-$ at pH 9 vs. WT at pH 7.2 |
|---|---|---|---|---|---|
| | pH 7.2 | pH 9 | pH 7.2 | pH 9 | |
| Pentamidine | 10 | 0.3125 | 0.3125 | 0.0097 | 1030 |
| EtBr | 5 | 0.078 | 0.3125 | 0.01 | 500 |
| Berberine | 60 | 3.75 | 7.5 | 0.23 | 260 |
| Palmatine | 200 | 12.5 | 50 | 0.78 | 256 |
| TPP | 15.6 | 0.48 | 1.98 | 0.12 | 130 |
| Benzalkonium Chloride | 0.67 | 0.08 | 0.16 | 0.0104 | 64 |
| Chlorhexidine | 0.5 | 0.06 | 0.125 | 0.0156 | 32 |
| Puromycin | 20 | 2.5 | 20 | 2.5 | 8 |
| Nofloxacin | 1.25 | 1.25 | 0.33 | 0.33 | 4 |

TABLE 2

Comparison of the effects of reserpine and a NorA disruption on antimicrobial resistance of S. aureus.

| Drugs | RN4222 (WT) MIC ($\mu$g/mL) | | KLE 820 (norA$^-$) MIC ($\mu$g/mL) | | Sensitivity$^c$ |
|---|---|---|---|---|---|
| | −R$^b$ | +R$^b$ | −R | +R | |
| EtBr$^a$ | 5 | 1.25 | 0.33 | 0.33 | 16 |
| TPP | 15.6 | 7.8 | 1.9 | 1.0 | 8 |
| Actiflavine | 20 | 10 | 2.5 | 2.5 | 8 |
| Nofloxacin | 1.25 | 0.67 | 0.33 | 0.33 | 4 |
| Ciprofloxacin | 0.67 | 0.33 | 0.16 | 0.16 | 4 |

$^a$TPP, tetraphenylphosphonium bromide; EtBr, ethidium bromide.
$^b$−R, no reserpine; +R, 20 $\mu$g/mL reserpine.
$^c$Sensitivity of norA$^-$ as compared to the wild type in the absence of reserpine.

TABLE 3

Synergistic Effect of Small Molecule MDR inhibitor (I) and high pH on MICs of antimicrobials in S. aureus.

| Substance ($\mu$g/mL) | pH 7 | pH 7 + I | Ratio | pH 9 | pH 9 + I | Ratio | Potentiation factor (pH 7/ (pH 9 + I)) |
|---|---|---|---|---|---|---|---|
| Berberine | 60 | 0.4 | 150 | 7.5 | 0.0125 | 600 | 4,800 |
| Palmatine | 100 | 1.6 | 62.5 | 25 | 0.08 | 312.5 | 1,250 |
| Pentamidine | 10 | 0.33 | 30 | 0.3 | 0.02 | 15 | 500 |
| Chlorhexidine | 0.5 | 0.06 | 8.3 | 0.12 | 0.0037 | 32 | 133 |
| Benzalkonium chloride | 0.67 | 0.08 | 8.3 | 0.16 | <0.005 | 32 | 134 |
| Sanguinarine | 2.5 | 0.67 | 3.7 | 1.25 | 0.15 | 8.3 | 16.6 |

All of the references and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

1. Strohl, W. R. (1997) *Biotechnology of Antibiotics* Strohl, W. R. (ed.) (Marcel Dekker, Inc., New York), pp. 1–47.
2. Desnottes, J. F. (1996) *Trends Biotechnol.* 14, 134–140.
3. Lewis, K. (1994) *Trends Biochem. Sci.* 19, 119–123.
4. Paulsen, I. T., Brown, M. H., & Skurray, R. A. (1996) *Microbiol. Rev.* 60, 575–608.
5. Bolhuis, H., van Veen, H. W., Poolman, B., Driessen, A. J. M., & Konings, W. N. (1997) *FEMS Microbiol. Rev.* 21, 55–84.
6. Lewis, K., Hooper, D., & Ouellette, M. (1997) *ASM News* 63, 605–610.
7. Kluytmans, J., van Belkum, A., & Verbrugh, H. (1997) *Clin. Microbiol. Rev.* 10, 505–520.
8. Neyfakh, A. A., Borsch, C. M., & Kaatz, G. W. (1993) *Antimicrob. Agents Chemother.* 37, 128–129.
9. Ng, E. Y., Trucksis, M., & Hooper, D. C. (1994) *Antimicrob. Agents Chemother.* 38, 1345–1355.
10. Gray, O., & Chang, S. (1981) *J. Bacteriol.* 145, 422–428.
11. Schenk, S. & Laddaga, R. A. 1992. *FEMS Microbiol. Lett.* 94, 133–138.
12. Tennent, J. M., Lyon, B. R., Midgley, M., Jones, I. G., Purewal, A. S., & Skurray, R. A. (1989) *J. Gen. Microbiol.* 135, 1–10.
13. Yamada, H., Kurose-Hamada, S., Fukuda, Y., Mitsuyama, J., Takahata, M., Minami, S., Watanabe, Y., & Narita, H. (1997) *Antimicrob. Agents Chemother.* 41, 2308–2309.
14. Neyfakh, A. A., Bidnenko, V. & Chen, L. B. (1991) *Proc. Natl. Acad. Sci. USA* 88, 4781–4785.
15. Padan, E., & Schuldiner, S. (1994) *Biochim. Biophys. Acta.* 1187, 206–210.
16. Skulachev, V. P. (1988) *Membrane Bioenergetics* (Springer-Verlag New York).
17. Grinius, L. L., Siehnel, R. J., & Morris, C. N. (1997) *FASEB J.* 11, 958.
18. Lomovskaya, O. & Lewis, K. (1992) *Proc. Natl. Acad. Sci. USA* 89, 8938–8942.
19. Ma, D., Cook, D. N., Alberti, M., Pon, H. Nikaido, & Hearst, J. E. (1993) *J. Bacteriol.* 175, 6299–6313.
20. Fleischmann, I. D. et al., (1995) *Science* 269, 496–512.
21. Ahmed, M., C. M. Borsch, S. S. Taylor, N. Vazquez-Laslop, & Neyfakh, A. A. (1994) *J. Biol. Chem.* 269, 28506–28513.
22. Lomovskaya, O., Lewis K., & Matin, A. (1995) *J. Bacteriol.* 177, 2328–1334.
23. Ahmed, M., Lyass, L., Markham, P. N., Taylor, S. S., Vazquez-Laslop, N., & Neyfakh, A. A. (1995) *J. Bacteriol.* 177, 3904–3910.
24. Ohki, R., & Murata, M. (1997) *J. Bacteriol.* 179, 1423–1427.
25. Krulwich, T. A., Ito, M., Gilmour, R., Sturr, M. G., Guffanti, A. A., & Hicks, D. B. (1996) *Biochim. Biophys. Acta.* 1275, 21–26.

We claim:

1. A method for increasing the accumulation of amphipathic weak bases, amphipathic cations, or both, in a cell, comprising the step of culturing said cell in the presence of said amphipathic weak bases, amphipathic cations, or both, and a multiple drug resistance inhibitor comprising reserpine in a medium with a pH of about 9.

2. The method of claim 1, wherein said cell is a bacterial cell.

3. The method of claim 1, wherein said cell is a fungal cell.

4. The method of claim 1, wherein said cell is a plant cell.

5. The method of claim 1, wherein said cell is an animal cell.

6. The method of claim 1, wherein said cell is a mammalian cell.

7. The method of claim 1, 2, 3, 4, 5, or 6, wherein at least one multiple drug resistance mechanism of said cell is attenuated.

8. The method of claim 7, wherein said multiple drug resistance mechanism is an efflux pump.

9. The method of claim 7, wherein said multiple drug resistance mechanism is an enzyme.

10. The method of claim 8 or 9, wherein said multiple drug resistance mechanism is attenuated by a gene knockout.

11. The method of claim 8 or 9, wherein said multiple drug resistance mechanism is attenuated by the suppression of expression of the gene(s) responsible for said mechanism.

12. The method of claim 1, 2, 3, 4, 5, 6, or 7, wherein said method is used in assay for biologically active compounds.

13. The method of claim 12, wherein said assay is used in a drug discovery program.

14. The method of claim 13, wherein said drug discovery program evaluates known compounds.

15. The method of claim 13, wherein said drug discovery program evaluates new compounds.

16. The method of claim 13, wherein said drug discovery program evaluates compounds for antibacterials, antifungals, cytotoxic agents, antineoplastic agents, antiproliferative agents, immunosuppressants, disinfectants, or antiseptics.

17. A formulation, comprising an amphipathic weak base, an amphipathic cation, or both; and a multiple drug resistance inhibitor comprising reserpine, wherein said weak base or said cation or both possesses antiseptic properties, disinfectant properties, or both; and wherein said formulation has a pH of about 9; and wherein the amphipathic weak base, amphipathic cation or both, and the multiple drug resistance inhibitor comprising reserpine exhibits a synergistic antiseptic and/or disinfectant effect.

18. The formulation of claim 17, wherein said formulation is a topical formulation.

19. The formulation of claim 18, wherein said formulation is a dentifrice.

20. The formulation of claim 18, wherein said formulation is an ointment.

21. A method for antisepsis, disinfection, or both, comprising the step of applying to a surface an effective amount of a formulation according to claim 16.

22. The method of claim 21, wherein said surface is inanimate.

23. The method of claim 22, wherein said surface is in a health care facility.

24. The method of claim 22, wherein said surface is in a domicile.

25. The method of claim 21, wherein said surface is animate.

26. The method of claim 25, wherein a plant comprises said surface.

27. The method of claim 25, wherein an animal comprises said surface.

28. The method of claim 25, wherein a mammal comprises said surface.

29. The method of claim 25, wherein a human comprises said surface.

30. The method of claim 25, 26, 27, 28, or 29, wherein a wound comprises said surface.

* * * * *

UNITED STATES PATENT AND TRADEMARK OFFICE
CERTIFICATE OF CORRECTION

PATENT NO.     : 6,410,041 B1
DATED          : June 25, 2002
INVENTOR(S)    : Lewis, K. and Hsieh P.C.

It is certified that error appears in the above-identified patent and that said Letters Patent is hereby corrected as shown below:

<u>Title page,</u>
Item [75], Inventors, replace "Peichun" with -- Pei-Chung --.

Signed and Sealed this

Eleventh Day of November, 2003

JAMES E. ROGAN
*Director of the United States Patent and Trademark Office*